United States Patent
Kurauchi et al.

(10) Patent No.: US 9,442,057 B2
(45) Date of Patent: Sep. 13, 2016

(54) METHOD OF MEASURING VISCOSITY AND VISCOSITY MEASURING APPARATUS

(75) Inventors: Nami Kurauchi, Kyoto (JP); Miki Nakamura, Kyoto (JP); Masanori Yasuda, Kyoto (JP)

(73) Assignee: Kyoto Electronics Manufacturing Co., Ltd., Kyoto (JP)

(*) Notice: Subject to any disclaimer, the term of this patent is extended or adjusted under 35 U.S.C. 154(b) by 1128 days.

(21) Appl. No.: 13/512,574

(22) PCT Filed: Feb. 17, 2011

(86) PCT No.: PCT/JP2011/000870
§ 371 (c)(1),
(2), (4) Date: May 29, 2012

(87) PCT Pub. No.: WO2011/102129
PCT Pub. Date: Aug. 25, 2011

(65) Prior Publication Data
US 2012/0239314 A1  Sep. 20, 2012

(30) Foreign Application Priority Data

Feb. 17, 2010 (JP) ................................. 2010-032375

(51) Int. Cl.
*G01N 11/14* (2006.01)
*G06F 19/00* (2011.01)

(52) U.S. Cl.
CPC ..................................... *G01N 11/14* (2013.01)

(58) Field of Classification Search
CPC .......................... B01F 15/00246; G01N 11/14
USPC ........................................... 702/54; 73/54.31
See application file for complete search history.

(56) References Cited

U.S. PATENT DOCUMENTS

2011/0036150 A1* 2/2011 Sakai .......................... 73/54.31

FOREIGN PATENT DOCUMENTS

| JP | 6-102164 A | 4/1994 |
| JP | 11-14471 A | 1/1999 |
| WO | WO 2009037636 A1 * | 3/2009 |
| WO | WO 2009/131185 A1 | 10/2009 |

OTHER PUBLICATIONS

Bano et al. "A viscosity and density meter with a magnetically suspended rotor", Review of Scientific Instruments, Nov. 2003, vol. 74, No. 11, pp. 4788-4793.*

* cited by examiner

*Primary Examiner* — John Breene
*Assistant Examiner* — Yaritza H Perez Bermudez
(74) *Attorney, Agent, or Firm* — Birch, Stewart, Kolasch & Birch, LLP (57) ABSTRACT

In a method of measuring a viscosity of a sample based on a rotation frequency $\Omega_S$ of a conductive rotator rotating by applying a rotating magnetic field from outside to the rotator set in a container containing the sample and a rotation frequency $\Omega_B$ of the magnetic field, a constant k1 having temperature dependency of an apparatus and a constant k2 not having the temperature dependency at each temperature are found by using a equation, $\eta 0 \Omega_S = k1(\Omega_B - \Omega_S) - k2$, where a viscosity $\eta 0$ at specific temperature is known, and then a value of viscosity measured at the specific temperature is corrected by means of the constants k1 and k2, the rotation frequency $\Omega_S$ of the rotator, and the rotation frequency $\Omega_B$ of the magnetic field. The constant k1 may employ the temperature dependency of electric conductivity of metal used to the rotator.

6 Claims, 8 Drawing Sheets

FIG. 8
(PRIOR ART)    Sample to be measured: Silicon Oil (5000cSt)

● True Value
○ Measurement Value (without Temperature Correction)

METHOD OF MEASURING VISCOSITY AND VISCOSITY MEASURING APPARATUS

TECHNICAL FIELD

The present invention relates to a method of measuring a viscosity and an apparatus thereof, and in particular, relates to temperature correction in the method wherein the viscosity is measured by applying a rotating magnetic field to a rotator.

BACKGROUND ART

Measuring a viscosity of a material is an indispensable technique for quality control, performance evaluation, material control, and research and development in manufacturing process of medicines, foods, coatings, inks, cosmetics, chemicals, papers, adhesives, fiber, plastics, beer, detergents, concrete admixture, and silicon or the like.

The methods of measuring viscosity are a method using a capillary tube, a method by contacting an oscillator with a sample, a method using a rotator, and so on.

The method using a rotator, one of the above-mentioned methods, is disclosed in International Publication No. WO 2009/131185 (International Patent Application No. PCT/JP2009/058089).

Specifically, it is configured so as to sink a conductive rotator (sphere) into a container containing a sample liquid, and apply a rotating magnetic field to the rotator from an outside of the container.

Under such configuration, when the rotating magnetic field is applied to the rotator, Lorentz force works between the electric current generated on the rotator and the rotating magnetic field, and the rotator rotates along with the rotating magnetic field. At this time, since the rotating velocity of the rotator delays depending on the viscosity of the sample from the rotating velocity of the rotating magnetic field, the viscosity can be calculated based on this relationship.

The difference between the rotating velocity of the rotator and the rotating velocity of the rotating magnetic field can be expressed by a linear equation having a specific slope. The slope of the linear equation becomes the viscosity.

PRIOR ART REFERENCE

Patent Literature 1: International Publication No. WO 2009/131185

SUMMARY OF INVENTION

Technical Problem

Figure 8:
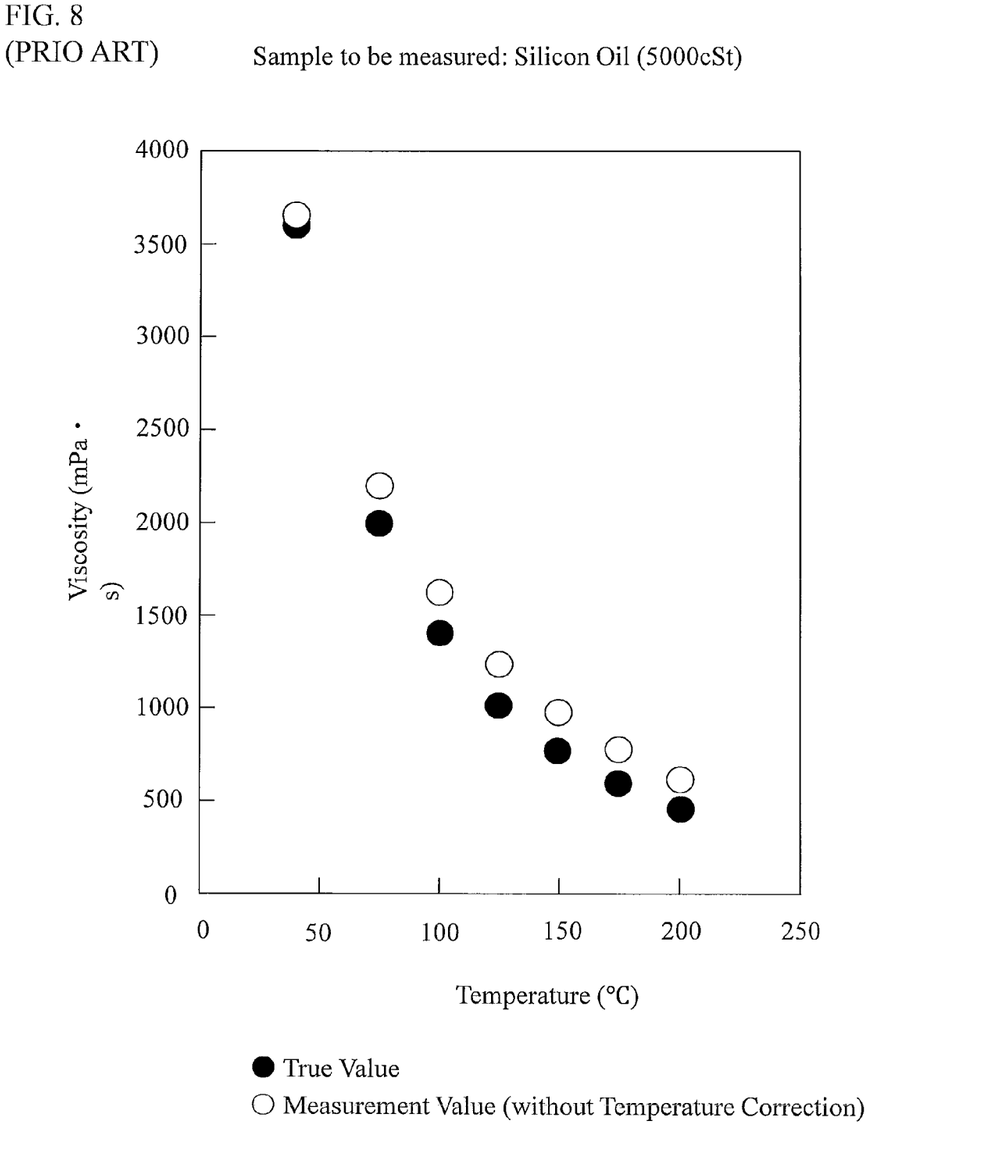
FIG. 8 is a graph showing a measurement result of a viscosity of silicon oil in a prior art.

The invention disclosed in WO 2009/131185 merely relates to the relationship between the rotating velocity of the rotator and the rotating velocity of the rotating magnetic field in a narrow range of temperature. In case of a wide range of temperature, an error is generated between a measured value and a true value, as shown in FIG. 8. FIG. 8 shows values of viscosity of silicon oil measured at the temperature from 40 degree C. to 200 degree C. It is noted that the measured value ○ is larger than the true value ●. This is caused that the provided magnetic field, a circuit for driving the magnetic field and the conductivity (electric conductivity) of the rotator change along with the temperature changes. As described later, the influence caused by the temperature dependency of the electric conductivity is extremely large.

The present invention is suggested in view of the above-mentioned conventional problems, and has an object to obtain the true value of viscosity by correcting the measured value of viscosity taking into consideration the change of apparatus property depending on temperature, and in particular, the influence caused by the conductivity change.

Solution to Problem

To achieve the above-mentioned object, the present invention employs following means. First, the present invention is a method of measuring a viscosity of a sample based on a rotation frequency $\Omega_S$ of a rotator rotating by applying a rotating magnetic field from outside to the rotator set in a container containing the sample, and a rotation frequency $\Omega_B$ of the rotating magnetic field.

By a following equation where a viscosity $\eta 0$ at specific temperature is known, $$\eta 0 \Omega_s = k1(\Omega_B - \Omega_S) - k2 \quad (k1, k2: \text{constant}) \tag{1}$$

a constant k1 having temperature dependency of an apparatus and a constant k2 are calculated at each temperature in advance. Using the calculated constants k1 and k2 (almost no change by the temperature change), the rotation frequency $\Omega_S$ of the rotator and the rotation frequency $\Omega_B$ of the magnetic field, a corrected viscosity $\eta$ at the specific temperature is calculated by a following equation (2).

$$\eta = \frac{k1(\Omega_B - \Omega_S) - k2}{\Omega_S} \tag{2}$$

Most of the influence upon the constant k1 having temperature dependency of the apparatus is the change of electric conductivity of rotator depending on the temperature change. The other influences, such as circuit, magnetic generator, and etc. can be ignored.

The temperature dependency of the constant k1 well coincides with the temperature dependency of the conductivity of the rotator. Accordingly, a value proportional to the conductivity of metal used to the rotator can be employed as the constant k1.

Therefore, it is understood that the measurement error of the viscosity caused by temperature may be corrected using the temperature dependency of the conductivity of metal used to the rotator.

Advantageous Effects of Invention

As described above, the measurement error of the viscosity caused by temperature can be corrected by the temperature dependency of the conductivity of rotator, and the correction process can be simplified.

DESCRIPTION OF EMBODIMENTS

First Embodiment of Invention

Figure 1:
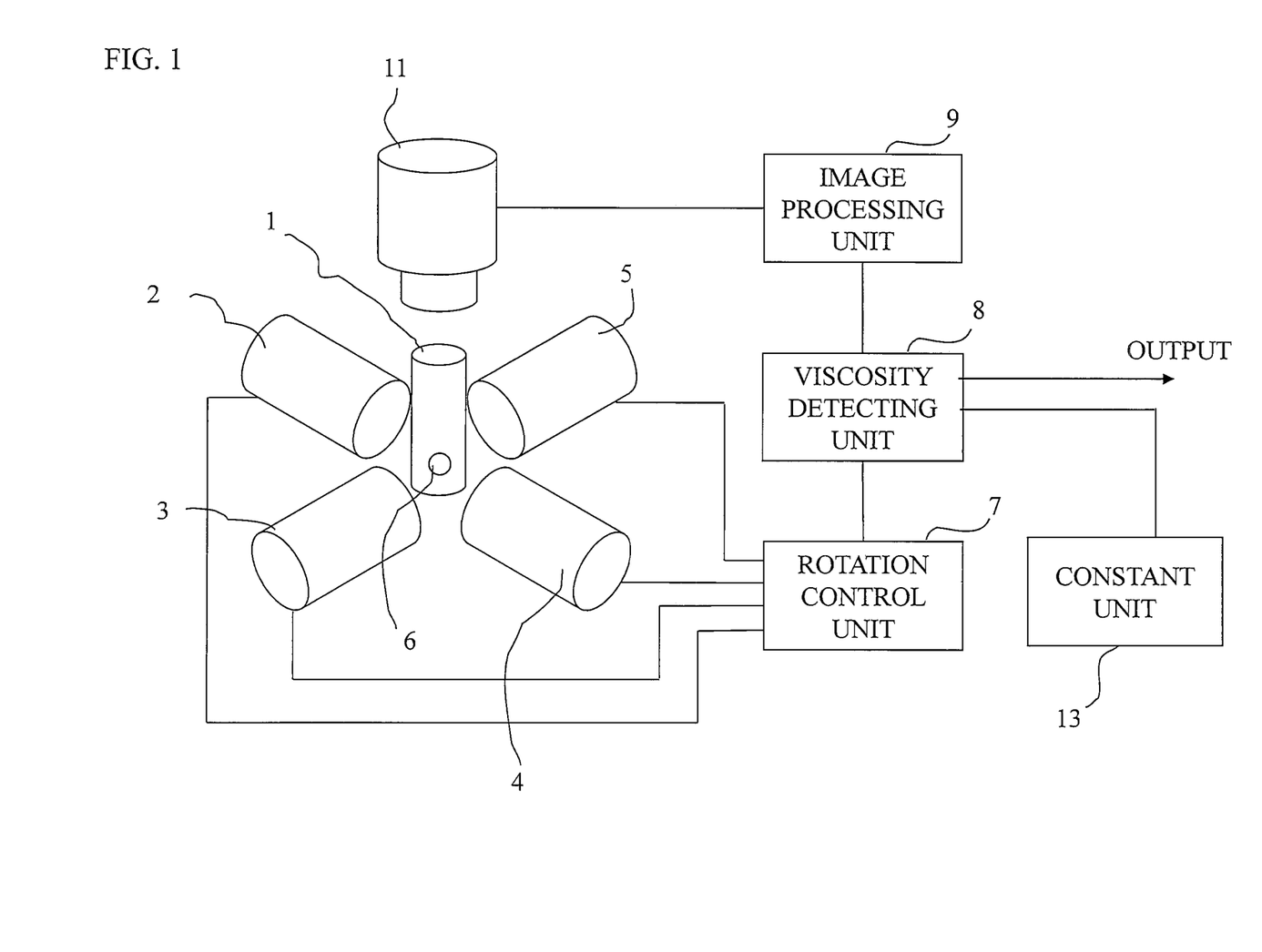
FIG. 1 is a conceptual diagram of an apparatus to which First Embodiment of the present invention is applied.

FIG. 1 is a diagram showing an outline of an apparatus to which First Embodiment of the present invention is applied.

A sample is contained in a container 1, and a conductive sphere (aluminum), that is a rotator 6, is placed in the container 1. The sphere is applied with a rotating magnetic field from an outside of the container 1. The magnetic filed may be applied under any configuration, however, an example shown in FIG. 1 is configured so that electromagnetic coils 2, . . . and 5 forming plural poles are placed surrounding the container 1, and each phase of electromagnetic coils 2, . . . and 5 is sequentially advanced in a direction at a specific speed by a rotation control unit 7.

Under such configuration, when the magnetic field is rotated, a current is induced into the conductive rotator 6 along with the rotation of the magnetic field, and the rotator 6 is rotated by Lorentz force working between the current and the magnetic field. Since the rotation frequency $\Omega_S$ of the rotator 6 depends on the viscosity of sample, a rotating state is captured by a camera 11, the captured images is processed by an image processing unit 9, and the rotation frequency $\Omega_S$ of rotator 6 is calculated. A viscosity detecting unit 8 is given the rotation frequency $\Omega_B$ of the rotating magnetic field applied to the electromagnetic coil by the rotation control unit 7, and also given the rotation frequency $\Omega_S$ of rotator 6 by the image processing unit 9. The viscosity is calculated based on the two rotation frequencies.

The method of calculating the viscosity is disclosed in the International Publication No. WO 2009/131185, so the details are not explained here. The relationship between "the difference between the rotating speed of the magnetic field and the rotating speed of the rotator" and "the rotating speed of the rotator" becomes a straight line relationship in a limited range of temperatures, and a slope of the straight line becomes a viscosity η.

The apparatus for the above-mentioned measurement has a temperature property. For instance, the magnetic property of coils and cores used to the rotating magnetic field and the circuits for applying the current to the coils are provided with the temperature properties. When the measurement is carried out at the temperature of 40 degrees C., the current flowing to the rotator 6 is different from the current flowing to the rotator 6 measured at the temperature of 200 degrees C. As explained with reference to FIG. 8, it is not perceived that the viscosity can be measured precisely under such conditions.

Here, where k1 and k2 are constants, the following relationship between the viscosity η0 and each rotation frequency $\Omega_S$ and $\Omega_B$ is established.

$$\eta 0 \Omega_s = k1(\Omega_B - \Omega_S) - k2 \qquad (1)$$

Figure 2:
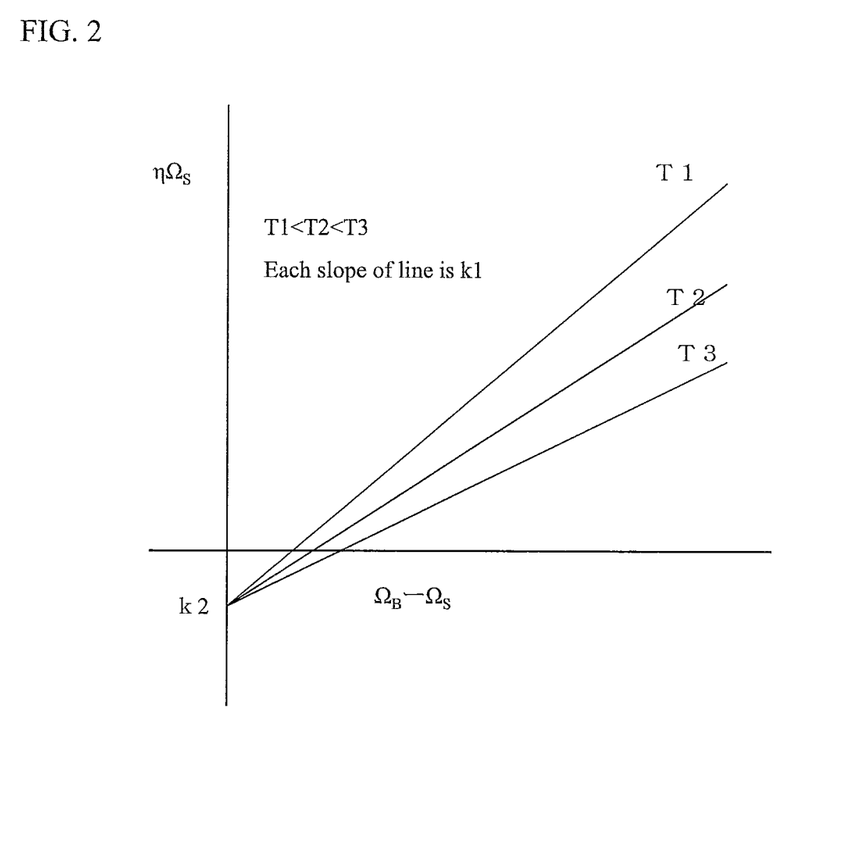
FIG. 2 is a graph showing a relationship among the rotation frequency of rotator, the rotation frequency of magnetic field, and a constant, at each temperature.
Figure 3:
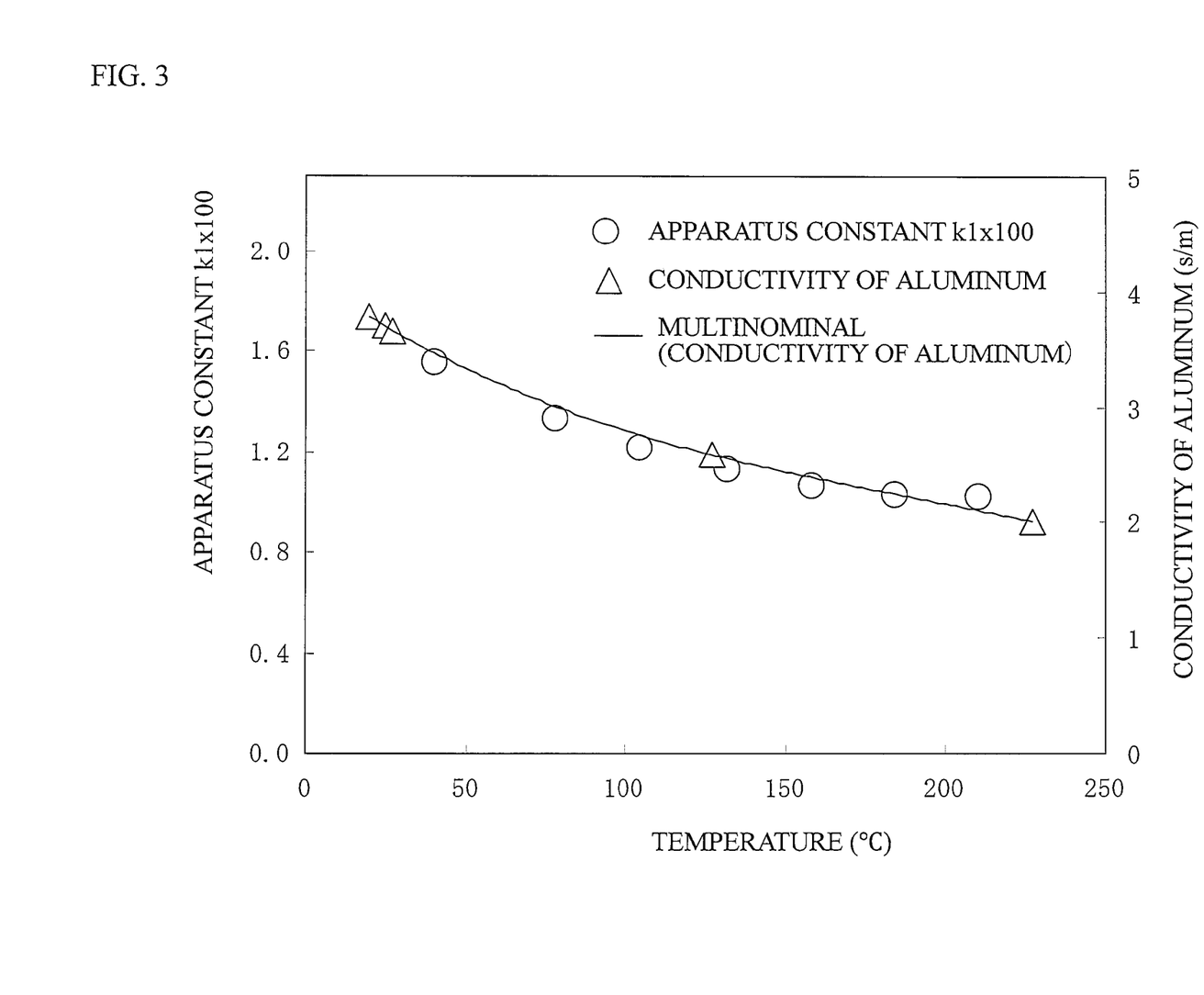
FIG. 3 is a graph showing a relationship between a constant k1 and a conductivity of aluminum in First Embodiment of the present invention.

When k1 and k2 at each temperature are found regarding a sample of which the viscosity η0 in a wide range of temperatures is known, the constant k2 is obtained as a fixed value wherein the temperature dependency can be almost ignored, and k1 is obtained as a group of straight lines, (the constant k1 is a slope of a straight line at each temperature), wherein k1 gets smaller as temperature T1, T2, . . . become higher, as shown in FIG. 2. Where the values of the constant k1 including the temperature dependency are represented in a graph based on the group of straight lines, these are shown as a mark ○ in FIG. 3. That is to say, it is possible to obtain the constant k1 that gets smaller as the temperature gets larger.

It is noted, by verifying the values of the constant k1, that the values of the constant k1 well coincide with the temperature dependency of the electric conductivity (Δ and a solid line in FIG. 3) of a metal (aluminum) used to the rotator 6, and the constant k1 closely corresponds to the electric conductivity of the metal used to the rotator 6. As also understood from the equation (1), the value of the constant k2 indicates a value of $\eta 0 \Omega_S$ when the rotation frequency $\Omega_S$ of the rotator 6 is the same as the rotation frequency $\Omega_B$ of the rotating magnetic field. At this time, the rotation frequency $\Omega_S$ of the rotator 6 is also considered to have no temperature dependency, and the temperature dependency of the constant k2 is not verified in an actual apparatus. Besides, the constant k2 is 0.002 in the apparatus used in this embodiment of the present invention.

The constants k1 and k2 do not have the substance dependency of sample, but these are a temperature dependency value (k1) having the temperature dependency of the apparatus (the electric conductivity of the rotator, in particular), and an apparatus property value (k2). Accordingly, the constants k1 and k2 can be found in advance by using the material of which viscosity is known.

The constants k1 and k2 found by using the sample having the known viscosity η0 as described above are stored beforehand in a memory provided to a constant unit 13.

Under such conditions, regarding the sample of which viscosity is unknown, the viscosity detecting unit 8 obtains the rotation frequency $\Omega_S$ of the rotator 6 and the rotation frequency $\Omega_B$ of the rotating magnetic field, and concurrently obtains the temperature dependency constant k1 and the constant k2 enough to ignore the temperature dependency. Further, the viscosity detecting unit 8 calculates a following equation modified from the equation (1), $$\eta = \frac{k1(\Omega_B - \Omega_S) - k2}{\Omega_S} \qquad (2)$$

and finds the viscosity η that is subjected to the temperature correction.

The constants k1 corresponding to each temperature and k2 may be stored as a table in the memory provided to the constant unit 13 as described above, but in this method, the memory is required to store limitless value of constant k1 corresponding to limitless temperature, in principle. Accordingly, the constant unit 13 may be configured so that the same metal as the rotator 6 is place on the same thermal environment as the measurement environment, and the electric conductivity of the metal used to the rotator is measured at the same time the rotation frequency $\Omega_B$ and $\Omega_S$ are detected, and then a value proportional to the measured electric conductivity value is given to the viscosity detecting unit 8. In this method, it is nevertheless to say that the constant k2 enough to ignore the temperature dependency is stored in the memory provided to the constant unit 13.

Figure 4:
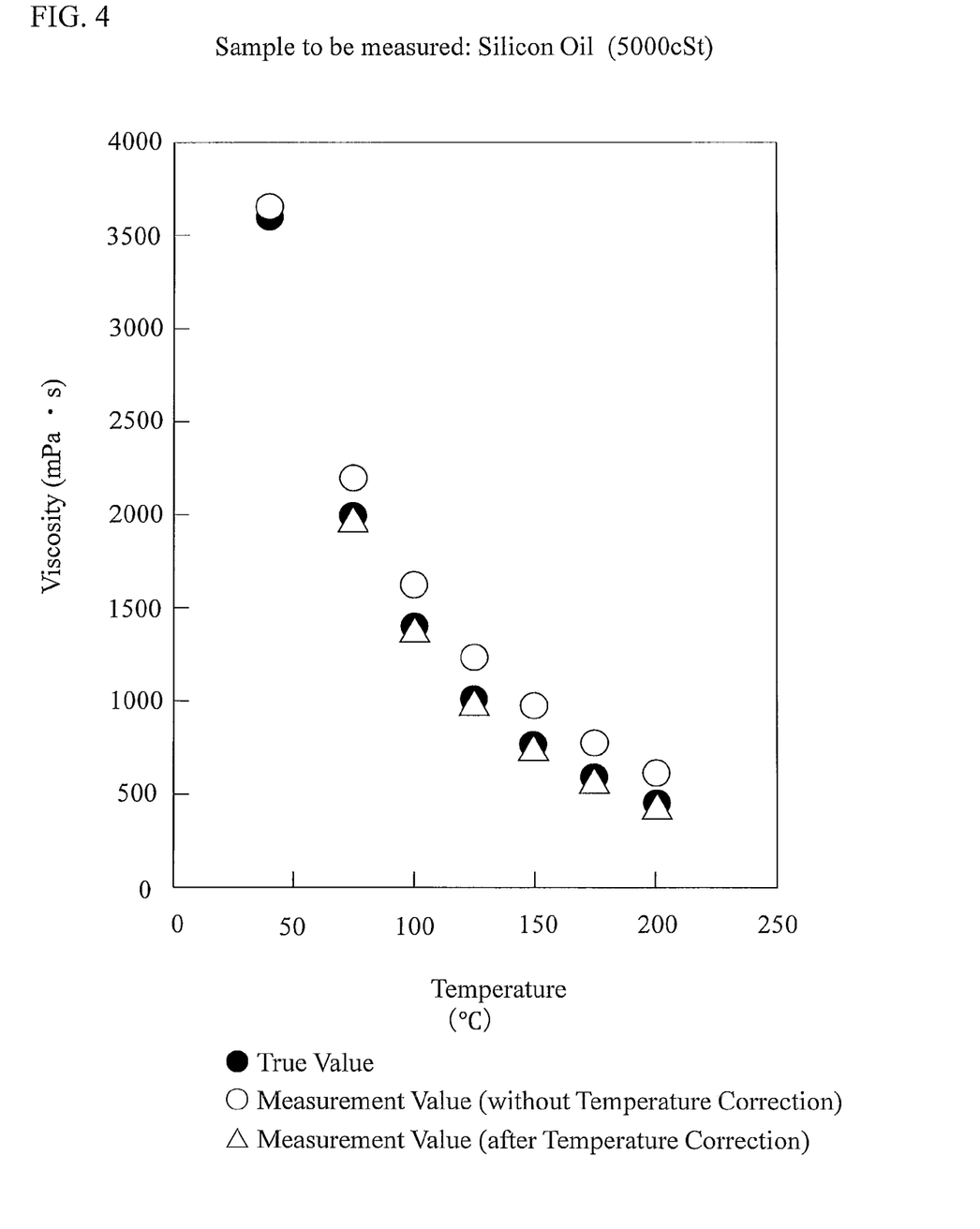
FIG. 4 is a graph showing a measurement result of a viscosity of silicon oil in First Embodiment of the present invention.

As the result of the above measurement, it is possible to obtain the viscosity η of the silicon oil that coincides with the true value ●, as shown by a mark Δ in FIG. 4. Therefore, it means that using the value proportional to the electric conductivity of the metal used to the rotator 6 as the constant k1 is right.

As described above, in the present invention, when the viscosity is calculated based on the rotation frequency of the rotator in the sample rotating by the rotating magnetic field, it is possible to obtain the true value of the viscosity by correcting the measured value for the error caused by the temperature dependency of the apparatus. In addition, the present invention can easily achieve the object by using the electric conductivity of the metal used to the rotator to the calculation.

The above explanation noted a case the metal used to the rotator 6 is aluminum, however, it is possible to provide the same effect in case of other metals (e.g., titanium).

Figure 5:
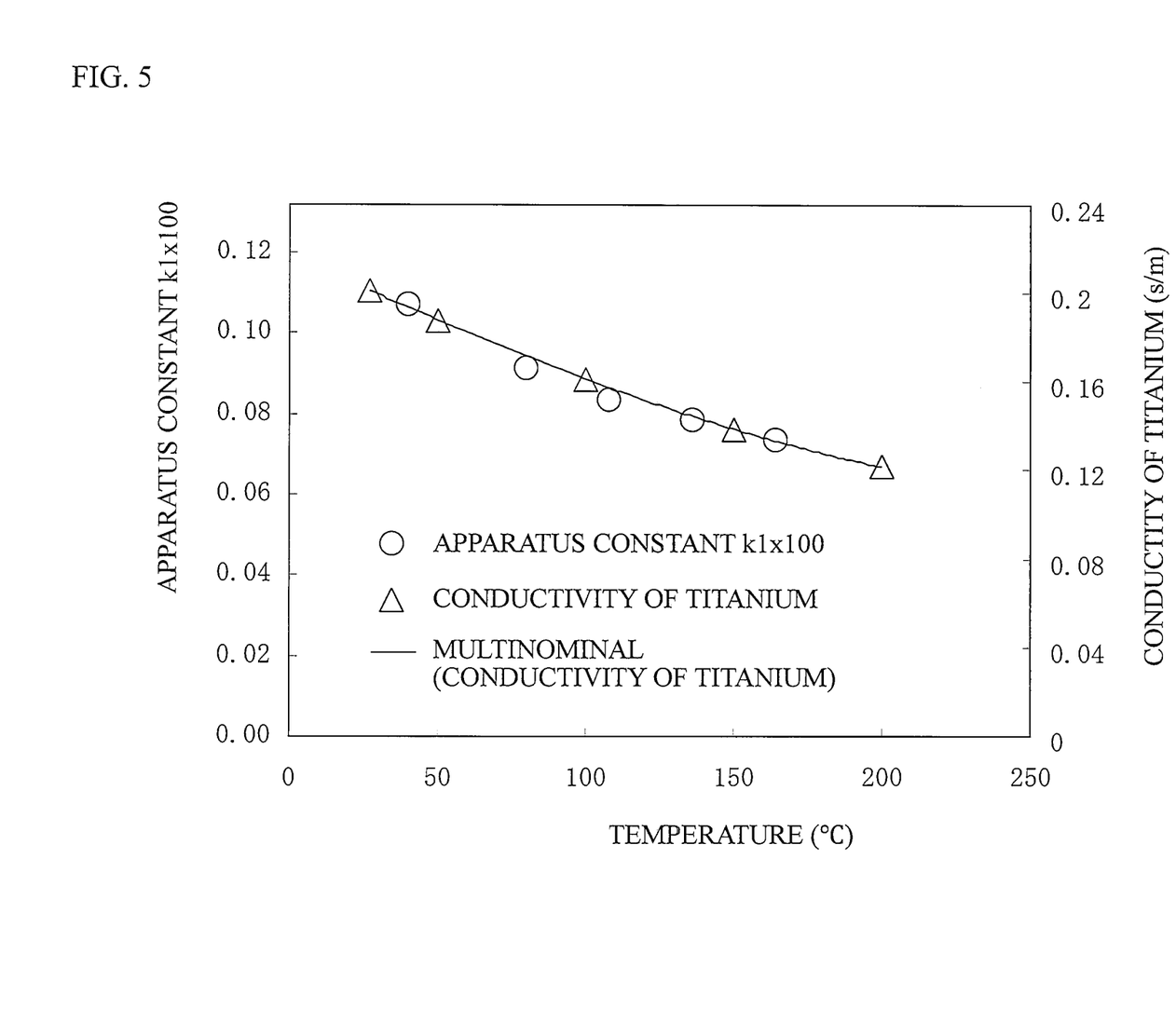
FIG. 5 is a graph showing a relationship between a constant k1 and a conductivity of titanium in First Embodiment of the present invention.

FIG. 5 is a graph showing the temperature dependency of the constant k1 when the metal used to the rotator 6 is titanium, and the temperature dependency of the electric conductivity of the titanium. As shown in FIG. 5, even if the metal used to the rotator 6 is titanium, the temperature dependency of the constant k1 (○ in FIG. 5) well coincides with the temperature dependency of the titanium conductivity (Δ and a solid line in FIG. 5). It is understood that the constant k1 is proportional to the electric conductivity of metal used to the rotator 6. Therefore, as described above, when the viscosity of the sample is calculated, the value proportional to the electric conductivity of metal used to the rotator is used to the calculation, whereby it is easy to correct the error caused by the temperature dependency of an apparatus that is included in the measured viscosity value, and the accurate viscosity can be calculated in a simple manner.

The above explanation noted a case the metal used to the rotator 6 is a pure metal made of one metal, such as aluminum, titanium or the like, however, it is possible to provide the same effect in case of alloy, such as aluminum alloy of which main component is aluminum, or titanium alloy of which main component is titanium.

Second Embodiment of Invention

Figure 6:
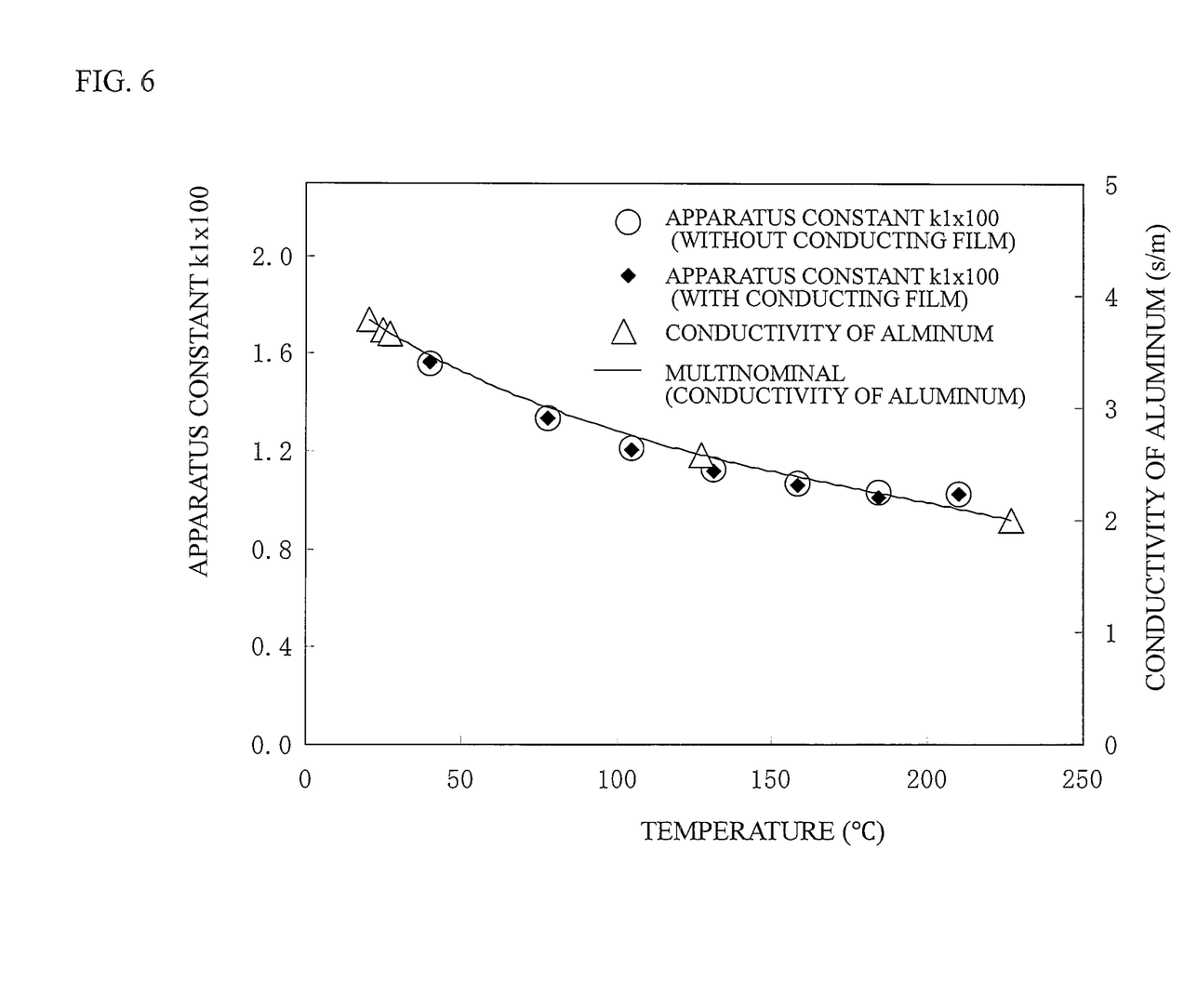
FIG. 6 is a graph showing a relationship among a conductivity of aluminum, a constant k1 in First embodiment, and a constant k1 in Second Embodiment of the present invention.
Figure 7:
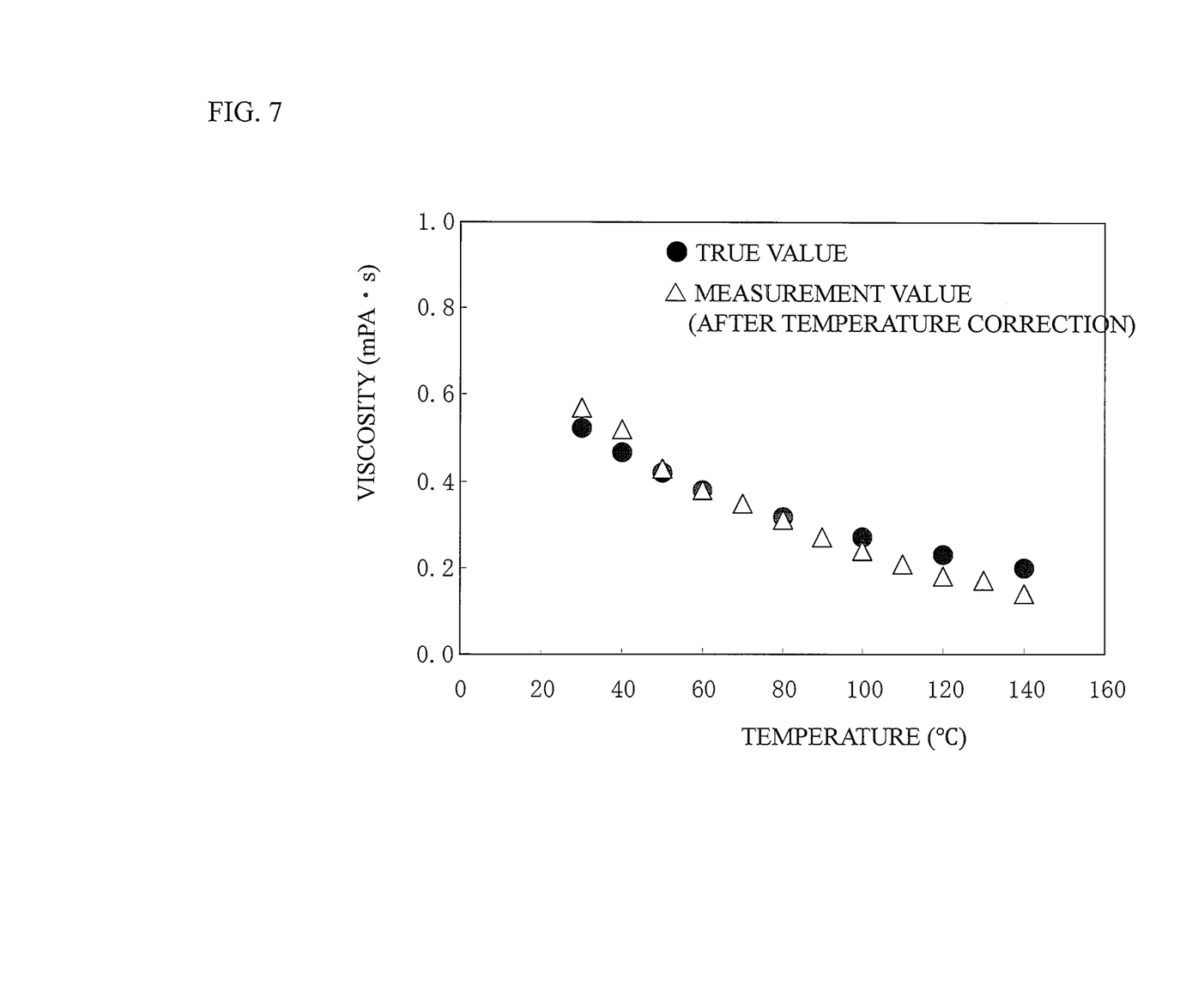
FIG. 7 is a graph showing a measurement result of a viscosity of toluene in Second Embodiment.

Referring to FIG. 6 and FIG. 7, here is explained that the apparatus in connection with Second Embodiment can easily correct the error caused by the temperature dependency of the apparatus. A distinct point of Second Embodiment as compared with First Embodiment is, when the viscosity of the sample easy to take a streaming electrification is measured, configured so as to discharge the electric charge generated in the sample to outside in some way. Since the other points are the same as First Embodiment, Second Embodiment is explained according to the figures used to the explanation of First Embodiment.

First Embodiment suggests a method and an apparatus of measuring the viscosity of silicon oil (Δ in FIG. 4) approximate to the true value (● in FIG. 4) by using the constant k1, the constant k2, the rotation frequency $\Omega_S$, and the rotation frequency $\Omega_B$. When the viscosity of a specific sample easy to take the streaming electrification, such as toluene, is measured by the apparatus and method described in first Embodiment, the streaming electrification is generated by the rotation of the rotator 6 during the viscosity measurement. Due to the electric charge of streaming electrification, the rotator 6 (conductive sphere) is adhered to an inner surface (wall surface) of the container 1, and the rotation of the rotator 6 is inhibited. It is not possible to accurately measure the viscosity value.

In Second embodiment of the present invention, it is configured so that, by providing the inner surface of the container 1 shown in FIG. 1 with the electrical conductivity, the electrical charge generated in the sample in the container is discharged to the outside. In order to provide the inner surface of the container 1 with the conductivity, the inner surface of the container 1 may be coated with the conducting film, or conductive wires (leads) may be inserted into the container 1, or a container having a nonmagnetic and conductive property may be used as the container 1, or the like.

By using the apparatus provided with the container of which inner surface is coated by the conducting film, the sample of which viscosity is known, and the equation (1), the constants k1 and k2 corresponding to each temperature are found in the same way as First Embodiment.

FIG. 6 is a graph showing the constant k1 for every temperature that is calculated by the apparatus (having the conducting film) in Second Embodiment, the constant k1 for every temperature that is calculated by the apparatus (without the conducting film) in First Embodiment, and the conductivity of the metal (aluminum) for every temperature that is used to the rotator 6 set in the container of the apparatus. As shown in FIG. 6, it is understood that the constant k1 in Second embodiment well coincides with the constant k1 in First Embodiment in spite of coating the conducting film on the inner surface of the container 1. Moreover, it is understood that, like First Embodiment, the temperature dependency of the constant k1 in Second Embodiment well coincides with the temperature dependency of the conductivity of the metal (aluminum) used to the rotator 6, and the constant k1 strongly depends on the conductivity of metal used to the rotator 6. Therefore, even in the apparatus in Second Embodiment, like First Embodiment, by using the value proportional to the conductivity of metal used to the rotator 6, it is easy to correct the error caused by the temperature dependency of the apparatus. Besides, the apparatus property value k2 at this time is 0.002, and it well coincides with the constant k2 in the apparatus in First Embodiment.

FIG. 7 is a graph showing a relationship between a measured value (Δ in FIG. 7) and a true value (● in FIG. 7) of viscosity of toluene, the measured value measured at from 30 degree C. to 140 degree C. by using the constant k1 (k1 shown in FIG. 6) and k2 calculated in the apparatus of Second Embodiment, the equation (2), the rotation frequency $\Omega_S$, and the rotation frequency $\Omega_B$. It is understood, as shown in FIG. 7, even if the viscosity of toluene easy to take the streaming electrification is measured by the apparatus provided with the container 1 of which the inner surface is given the conductivity, it is possible to obtain the measured value of viscosity (Δ in FIG. 7) of toluene approximate to the true value (● in FIG. 7).

As described above, in Second Embodiment, even if the sample is easy to take the streaming electrification, (e.g. toluene), when the apparatus employs the container 1 so as to discharge the electric charge generated in the sample, it is easy to obtain the measured value (Δ in FIG. 7) that more coincides with the true value (● in FIG. 7). It means that, in case where the inner wall of the container 1 is coated with the metal film, it is sure to correct the error caused by the temperature dependency of the apparatus by using the constants k1 and k2 calculated according to the equation (1) and the sample having the known viscosity together with the equation (2).

As shown in FIG. 6 and FIG. 7, Second Embodiment noted that the viscosity of toluene easy to take the streaming electrification can be measured with high accuracy when the metal used to the rotator 6 is aluminum. When the metal of the rotator 6 is titanium, however, it is possible to obtain the same result as above. Specifically, when the metal of the rotator 6 is titanium, the temperature dependency of the constant k1 calculated using the container 1 of which inner surface is coated with the conducting film well coincides with the temperature dependency of the conductivity of the metal of the rotator (titanium), and the constant k1 strongly depends on the temperature dependency of the metal of the rotator 6. Therefore, the value k1 proportional to the conductivity of metal of the rotator 6, the apparatus property value k2, and the equation (2) are used to the calculation, so that the viscosity of sample easy to take the streaming electrification can be measured with high accuracy.

Additionally, Second Embodiment employs the method of coating the inner surface of the container 1 with the conducting film in order to have the inner surface of the container the conductivity, however, the method of coating with the conducting film may be a silver mirror reaction, a non-electroplating, a vapor deposition, or the like.

INDUSTRIAL APPLICABILITY

The present invention can obtain the viscosity without depending on the temperature of the measuring environment, so that the industrial applicability is very large.

REFERENCE SIGNS LIST

Container
2 . . . 5 Rotating Magnetic Field
6 Rotator
7 Rotation Control Unit
8 Viscosity Detecting Unit
9 Image Processing Unit
13 Constant Unit

The invention claimed is:

1. A method of measuring a viscosity of a sample based on a rotation frequency $\Omega_s$ of a rotator rotating by applying a rotating magnetic field from outside to the rotator set in a container containing the sample, and a rotation frequency $\Omega_B$ of the rotating magnetic field, comprising steps of:

using the relation of a known viscosity $\eta_0$ of the sample at a specific temperature and the rotation frequencies $\Omega_s$ and $\Omega_B$ is expressed as, $\eta 0 \Omega_s = k1(\Omega_B - \Omega_s) - k2$, by calculating a constant k1 having temperature dependency of an apparatus and defining a constant k2 without the temperature dependency that is a product of the viscosity $\eta 0$ and the rotation frequency $\Omega_s$ when the rotation frequency $\Omega_s$ of the rotator is the same as the rotation frequency $\Omega_B$ of the rotation magnetic field, and storing the constants k1 for different temperatures and the constant k2 in a memory; finding the rotation frequency $\Omega_s$ of the rotator by an image processing unit processing a rotating state that a camera captures;

finding the rotation frequency $\Omega_B$ of the rotating magnetic field by a rotation control unit that applies the rotating magnetic field from the outside of the container; and using the rotation frequency $\Omega_s$ of the rotator, the rotation frequency $\Omega_B$ of the magnetic field, and the constants k1 and k2 from the memory, using the equation:

$$\eta = \frac{k1(\Omega_B - \Omega_S) - k2}{\Omega_S}$$

to calculate a viscosity $\eta$ of the sample at the specific temperature by a viscosity detecting unit.

2. The method of measuring a viscosity of a sample according to claim 1, wherein the constant k1 employs a value of the temperature dependency of electric conductivity of the rotator.

3. The method of claim 1 wherein the memory is included in a constant unit.

4. An apparatus for measuring a viscosity of a sample based on a rotation frequency $\Omega_s$ of a rotator rotating by applying a rotating magnetic field from outside to the rotator set in a container containing the sample, and a rotation frequency $\Omega_B$ of the rotating magnetic field, comprising:

an image processing unit for finding the rotation frequency $\Omega_s$ of the rotator by processing a rotating state that a camera captures;

a rotation control unit for finding the rotation $\Omega_B$ of the rotating magnetic field by applying the rotating magnetic field from the outside of the container;

a constant unit, where a relation of a known viscosity $\eta_0$ of the sample at a specific temperature and the rotation frequencies $\Omega_s$ and $\Omega_B$ is expressed as, $\eta 0 \Omega_s = k1(\Omega_B - \Omega_s) - k2$, for calculating a constant k1 having temperature dependency of an apparatus and defining a constant k2 without the temperature dependency that is a product of the viscosity $\eta 0$ and the rotation frequency $\Omega_s$ when the rotation frequency $\Omega_s$ of the rotator is the same as the rotation frequency $\Omega_B$ of the rotation magnetic field, and storing the constants k1 for different temperatures and the constant k2 in a memory; and a viscosity detecting unit, using the rotation frequency $\Omega_s$ of the rotator, the rotation frequency $\Omega_B$ of the magnetic field, and the constants k1 and k2 from the memory of the constant unit, using the equation:

$$\eta = \frac{k1(\Omega_B - \Omega_S) - k2}{\Omega_S}$$

to calculate a viscosity $\eta$ of the sample at the specific temperature.

5. The apparatus for measuring a viscosity of a sample according to claim 4, wherein the constant k1 employs a value of the temperature dependency of electric conductivity of the rotator.

6. The apparatus of claim 4 wherein said constant unit determines the constant value using a table stored in the memory.

* * * * *